US008036868B2

(12) United States Patent
Zeineh et al.

(10) Patent No.: US 8,036,868 B2
(45) Date of Patent: Oct. 11, 2011

(54) INTERGRATED SYSTEMS AND METHODS OF VIRTUAL OR LIVE MICROSCOPE SLIDE PRESENTATION

(75) Inventors: Jack A. Zeineh, Newport Beach, CA (US); Usman Rashid, Irvine, CA (US); Rui-Tao Dong, Mission Viejo, CA (US)

(73) Assignee: Carl Zeiss MicroImaging GmbH, Jena (DE)

( * ) Notice: Subject to any disclaimer, the term of this patent is extended or adjusted under 35 U.S.C. 154(b) by 0 days.

(21) Appl. No.: 12/584,831

(22) Filed: Sep. 11, 2009

(65) Prior Publication Data

US 2010/0073472 A1     Mar. 25, 2010

Related U.S. Application Data

(63) Continuation of application No. 10/620,016, filed on Jul. 14, 2003, now abandoned, which is a continuation-in-part of application No. 10/448,913, filed on May 30, 2003, now Pat. No. 7,224,839, which is a continuation of application No. 09/323,371, filed on Jun. 1, 1999, now Pat. No. 6,606,413.

(60) Provisional application No. 60/087,523, filed on Jun. 1, 1998.

(51) Int. Cl.
G06G 7/58 (2006.01)

(52) U.S. Cl. ............. 703/11; 702/19; 382/128; 382/305

(58) Field of Classification Search ........................ None
See application file for complete search history.

(56) References Cited

U.S. PATENT DOCUMENTS

| 4,742,558 | A |  | 5/1988 | Ishibashi et al. |
|---|---|---|---|---|
| 4,760,385 | A |  | 7/1988 | Jansson et al. |
| 4,922,909 | A |  | 5/1990 | Little et al. |
| 5,123,056 | A |  | 6/1992 | Wilson |
| 5,216,596 | A |  | 6/1993 | Weinstein |
| 5,252,487 | A |  | 10/1993 | Bacus et al. |
| 5,257,182 | A |  | 10/1993 | Luck et al. |
| 5,297,034 | A | * | 3/1994 | Weinstein ............... 382/128 |
| 5,329,616 | A |  | 7/1994 | Silverbrook |
| 5,428,690 | A |  | 6/1995 | Bacus et al. |
| 5,440,343 | A |  | 8/1995 | Parulski et al. |
| 5,499,097 | A |  | 3/1996 | Ortyn et al. |
| 5,602,674 | A |  | 2/1997 | Weissman et al. |
| 5,619,032 | A |  | 4/1997 | Kasdan |
| 5,625,765 | A |  | 4/1997 | Ellenby et al. |
| 5,626,144 | A |  | 5/1997 | Tacklind et al. |
| 5,655,028 | A |  | 8/1997 | Soll et al. |
| 5,655,029 | A |  | 8/1997 | Rutenberg et al. |
| 5,703,714 | A | * | 12/1997 | Kojima ............... 359/368 |
| 5,790,710 | A |  | 8/1998 | Price et al. |
| 5,793,969 | A |  | 8/1998 | Kamentsky et al. |
| 5,797,130 | A |  | 8/1998 | Nelson et al. |
| 5,818,637 | A |  | 10/1998 | Hoover et al. |
| 5,836,877 | A |  | 11/1998 | Zavislan |
| 5,838,837 | A |  | 11/1998 | Hirosawa et al. |
| 5,883,982 | A |  | 3/1999 | Riley et al. |
| 5,920,657 | A |  | 7/1999 | Bender et al. |
| 5,940,834 | A |  | 8/1999 | Pinard et al. |
| 5,968,731 | A |  | 10/1999 | Layne et al. |
| 5,991,461 | A |  | 11/1999 | Schmucker et al. |
| 5,991,729 | A |  | 11/1999 | Barry et al. |
| 6,006,191 | A |  | 12/1999 | DiRenzo |
| 6,014,451 | A |  | 1/2000 | Berry et al. |
| 6,031,475 | A |  | 2/2000 | Combe et al. |
| 6,031,930 | A |  | 2/2000 | Bacus et al. |
| 6,043,475 | A |  | 3/2000 | Shimada et al. |
| 6,075,900 | A |  | 6/2000 | Sakazawa et al. |
| 6,078,681 | A |  | 6/2000 | Silver |
| 6,101,265 | A |  | 8/2000 | Bacus et al. |
| 6,122,396 | A |  | 9/2000 | King et al. |
| 6,137,915 | A |  | 10/2000 | Chai |
| 6,208,374 | B1 |  | 3/2001 | Clinch |
| 6,226,392 | B1 |  | 5/2001 | Bacus et al. |
| 6,252,989 | B1 |  | 6/2001 | Geisler et al. |
| 6,259,080 | B1 |  | 7/2001 | Li et al. |
| 6,272,235 | B1 |  | 8/2001 | Bacus et al. |
| 6,396,941 | B1 |  | 5/2002 | Bacus et al. |
| 6,404,906 | B2 |  | 6/2002 | Bacus et al. |
| 6,466,690 | B2 |  | 10/2002 | Bacus et al. |
| 6,522,774 | B1 |  | 2/2003 | Bacus et al. |
| 6,606,413 | B1 |  | 8/2003 | Zeineh |
| 6,674,881 | B2 |  | 1/2004 | Bacus et al. |
| 6,674,884 | B2 |  | 1/2004 | Bacus et al. |
| 6,711,283 | B1 |  | 3/2004 | Soenksen |

(Continued)

FOREIGN PATENT DOCUMENTS

DE          19625862          1/1998

(Continued)

OTHER PUBLICATIONS

Wray et al., "The design and use of a computer-based digital image acquisition, management, and communications system for conferencing in pathology", 1995, Archives D Anatomie et de Cytologie Pathologiques, vol. 43, No. 4, abstract.*

(Continued)

*Primary Examiner* — Carolyn L. Smith
(74) *Attorney, Agent, or Firm* — Patterson Thuente Christensen Pedersen, P.A.

(57) ABSTRACT

A method for creating a virtual slide is provided. A virtual slide is a digital representation of an area of interest of a microscopic slide. One method is to use a motorized microscope that can move a specimen with respect to a microscopic objective. With such a system, one can capture one or more images through a microscopic objective, such that a region of interest is imaged. Each image is then joined together to form a composite or "virtual image." In one embodiment, after a virtual slide is created, a user may fully utilize the full capabilities of the remote microscope. Among these capabilities is a set of "optical objectives" and "virtual objectives." Optical objectives are images created by digitizing an image through a microscopic objective in real time. Virtual objectives are digitally created magnifications created by utilizing the existing virtual slide data to digitally create a field of view.

8 Claims, 2 Drawing Sheets

U.S. PATENT DOCUMENTS

| | | |
|---|---|---|
| 6,775,402 B2 | 8/2004 | Bacus et al. |
| 6,920,239 B2 | 7/2005 | Douglass et al. |
| 7,224,839 B2 | 5/2007 | Zeineh |
| 7,272,252 B2 | 9/2007 | Torre-Bueno et al. |
| 7,391,894 B2 | 6/2008 | Zeineh |
| 7,505,616 B2 | 3/2009 | Zeineh |
| 2002/0061127 A1 | 5/2002 | Bacus et al. |
| 2002/0090127 A1 | 7/2002 | Wetzel et al. |
| 2002/0135678 A1 | 9/2002 | Bacus et al. |
| 2002/0149628 A1 | 10/2002 | Smith et al. |
| 2003/0012420 A1 | 1/2003 | Verwoerd et al. |
| 2003/0039384 A1 | 2/2003 | Bacus et al. |
| 2003/0090127 A1 | 5/2003 | Saeki |
| 2003/0112330 A1 | 6/2003 | Yuri et al. |
| 2003/0123717 A1 | 7/2003 | Bacus et al. |
| 2003/0138139 A1 | 7/2003 | Strom |
| 2003/0184730 A1 | 10/2003 | Price |
| 2003/0210262 A1 | 11/2003 | Gahm et al. |
| 2003/0228053 A1 | 12/2003 | Li et al. |
| 2004/0004614 A1 | 1/2004 | Bacus et al. |
| 2004/0047033 A1 | 3/2004 | Nakagawa |
| 2004/0083085 A1 | 4/2004 | Zeineh et al. |
| 2004/0136582 A1 | 7/2004 | Bacus et al. |
| 2004/0141637 A1 | 7/2004 | Bacus et al. |
| 2004/0236773 A1 | 11/2004 | Bacus et al. |
| 2006/0276974 A1 | 12/2006 | Zeineh et al. |
| 2008/0232663 A1 | 9/2008 | Zeineh |
| 2010/0034437 A1 | 2/2010 | Zeineh |
| 2010/0067759 A1 | 3/2010 | Zeineh |

FOREIGN PATENT DOCUMENTS

| | | |
|---|---|---|
| DE | 19707026 | 9/1998 |
| JP | 02272413 | 7/1990 |
| JP | 09117417 | 10/1995 |
| JP | 09037232 | 2/1997 |
| JP | 09051498 | 2/1997 |
| JP | 10186238 | 7/1998 |
| JP | 10224783 | 8/1998 |
| JP | 10274741 | 10/1998 |
| JP | 11009556 | 1/1999 |
| WO | WO 98/01999 | 1/1998 |
| WO | WO 98/08342 | 2/1998 |
| WO | WO 98/39728 | 9/1998 |
| WO | WO 98/41022 | 9/1998 |
| WO | WO 99/13360 | 3/1999 |
| WO | WO 99/13400 | 3/1999 |
| WO | WO 99/14882 | 3/1999 |
| WO | WO 02/50759 | 6/2002 |
| WO | WO 02/056084 | 7/2002 |
| WO | WO 02/056256 | 7/2002 |

OTHER PUBLICATIONS

Telepathology and the Networking of Pathology Diagnostic Services, by Ronald S. Weinstein, M.D., et al., published in Arch Pathol. Lab Med., vol. III, Jul. 1987.

"Aspects of Standardization in Telepathology", by K. Kayser, P. Schwarzmann, Department of Pathology, Thoraxklinik, Heidelberg, Institute of Applied Electronics, University of Stuttgart, Germany, 1992.

"The Distributed Laboratory", SIGraph '92 Showcase, vol. 35, No. 6, Communications of the ACM, Jun. 1992.

"Progress in Telepathology", K. Kayser, Department of Pathology, Thoraxklinik, D-6900 Heidelberg, Germany, 1993.

"Telemicroscopy". By G.Y. Fan, P.J. Mercurio, S.J. Young, and M.H. Ellisman, Ultramicroscopy, 1993.

Telepathology with an Integrated Service Digital Network—A New Tool for Image Transfer in Surgical Pathology: A Preliminary Report, by Martin Oberholzer, M.D., et al., Department of Pathology and the Computer Centre and Institute of Informatics, University of Basel, Basel, Switzerland, 1993.

"Telepathlogy is Available for Transplantation-Pathology: Experience in Japan Using an Integrated, Low-Cost, and High-Quality System", by Hisas Ito, et al., from Modern Pathology, vol. 7, No. 7, p. 801, 1994.

"Compendium on the Computerized Cytology and Histology Laboratory", by George L. Wied, et al., Tutorials of Cytology, Chicago, Illinois, U.S.A., 1994.

"Telepathology", by Shigeru Arai, M.D., Department of Pathology, Yamagata University School of Medicine, Yamagata 990-23, Japan, 1995.

"Telepathology: Frozen Section Diagnosis at a Distance", by M. Oberholzer, et al., Springer-Verlag, 1995.

Telepathology: Expert Center Cooperation in the Field of Anatomic Pathology, by James O'D. McGee, et al., The Journal of Pathology, vol. 175, p. 152A, 1995.

"Teleradiology/Telepathology Requirements and Implementation", Seong K. Mun, et al., Journal of Medical Systems, vol. 19, No. 2, pp. 153-164, 1995.

"Expert Consultation by Use of Telepathology—The Heidelberg Experiences", by Klaus Kayser, et al., published in Analytical Cellular Pathology, No. 9, pp. 53-60, 1995.

"Quick Return Service of the Surgical Pathology", by Seiichi Tamai, M.D., 43, pp. 1017-1023, 1995.

The Validity of Intraoperative Frozem Section Diagnosis Based on Video-microscopy (Telepathology), published in General & Diagnostic Pathology, 141, pp. 105-110, 1995.

"Telepathology: A Tool to Aid in Diagnosis and Quality Assurance in Cervicovaginal Cytology", by C. Marsan, et al., published in Cytopathology, 6, pp. 339-342, 1995.

"Apport de l'infomratique et de la telephathologie en anatomocytopathologie cancerologique", by Ed Martin, et al., published in Bull. Cancer, 82, Supp. 5, 565s-568s, 1995.

"Telemedecine Et Responsabilitie Medicale", by F.A. Allaert, et al., published in Arch. Anat. Cytol. Path., 43, n 4, pp. 200-205, 1995.

A Contribution to the Quantitative Analysis of Transmitted Images, by A. Dubur, et al., published in Arch. Anat. Cytol. Path., 43, n 4, pp. 268-270, 1995.

"Telepathology: Clinical Assessment of an International Network", by A. Bhattachatyya, et al., International Academy of Pathology, 84.sup.th Annual Meeting, Toronto Sheraton Center, Mar. 11-17, 1995, published in Modern Pathology, vol. 8, No. 1, p. 162A, Jan. 1995.

"Evaluation of High Resolution Diagnostic Images After Wavelet Based Image Compression", by L.A. Langford, et al., published in The FASEB Journal, vol. 9, No. 4, p. A1067, Mar. 10, 1995.

Microscopy ListServer Archives, E-mail from Bram Koster, printed from http://www.msa,microscopy.com/MicroscopyListserver/MicroscopyArchives.htm-l, Jun. 22, 1995.

"Telemedicine: Delivering Medical Expertise Across the State and Around the World", by Henry A. Swett, M.D., et al., published in Connecticut Medicine, vol. 59, No. 10, Oct. 1995.

"Remote Microscope for Inspection of Integrated Circuits", by James T. Kao, Massachusetts Institute of Technology, Sep. 1995.

"Evaluation of a Telepathology System Between Boston (USA) and Dijon (France): Glass Slides Versus Telediagnostic TV-Monitor", by F.A. Allaert, et al., Nineteenth Annual Symposium on Computer Applications in Medical Care, Oct. 28-Nov. 1, 1995.

"Fastest is Always Best and Other PACS Fallacies", by Mike Cannavo, published in Health Management Technology, Nov. 1995.

"A New Paradigm—Multi-User Scanning Electron Microscopy", by L.S. Chumbley, et al., JOM, 47(9), pp. 13-17, 1995, printed on Jun. 14, 2003, from Web site http://www.tims.org/pubs/journals/JOM/9509/Chumbley-9509.html.

"Automated Digital Image Mosaicing for Telemicroscopy", by Steven T. Peltier, University of California, San Diego, 1996.

Factors Influencing Distant Tele-evaluation in Cytology Pathology, Conventional Radiology and Mammography, by Olga Ferrer Roca, et al., Published in Analytical Cellular Pathology, 10, pp. 13-23, 1996.

"Quantitative DNA Ploidy Analysis of Breast Carcinoma: A Study of the Effects of Joint Photographer Expert Group (JPEG) Compression on DNA Ploidy Images", by Laura A. Phillips, M.L.T., et al., Diagnostic Cytopathology, vol. 15, No. 3, pp. 231-236, 1996.

"Strategie d'utilisation du telediagnostic et de la banque d'images", by G. Flandrin, Ann. Pathol., 16, n 3, p. 155-158, 1996.

Telepathology Through the Internet, by V. Della Mea, et al., published in the Journal of Telemedicine and Telecare, vol. 2, Supp. 1, 1996.

"Frozen-section Services by Telepathology: Experience of 100 Cases in the San-in District, Japan", by Hironobu Adachi, et al., published in Pathology International, 46, pp. 436-441, 1996.

"Evaluating Image for International Consortium for Internet Telepathology Project (ICIT)", by Y. Yagi, et al., published in Blackwell Scientific Publication for Pathology Interational, 46 (Suppl. 1), Japanese Society of Pathology, 1996.

"Telemedizin", by K. Kayser, published in Wien Klin Wochenschr, 108/17, pp. 532-540, 1996.

"Image Analysis (IA) of Skin Specimens: The Application of Telepathology (TP) to Frozen Section Evaluation", by L.B. Jacobs, et al., published in Modern Pathology, vol. 9, No. 1, p. 172A, Jan. 1996.

"Diagnostic Accuracy of an Interactive Telepathology System", by R.O. Rainer, et al., published in Modern Pathology, vol. 9, No. 1, Jan. 1996.

"Telepathology: Utility, Diagnostic Accuracy and Interobserver Variability on a Difficult Case Consultation Service", by S.S. Raab, et al., published in Modern Pathology, vol. 9, No. 1, p. 166A, Jan. 1996.

"Telepathology Diagnoses of Prostate Needle Biopsies", by M.H. Weinstein, et al., published in Modern Pathology, vol. 9, No. 1, p. 85A, Jan. 1996.

"Static Image Telepathology in Perspective", by Ronald S. Weinstein, M.D., published in Human Pathology, vol. 27, No. 2. pp. 99-101, Feb. 1996.

"Telepathology Diagnosis by Means of Digital Still Images: An International Validation Study", by David S. Weinberg, M.D., et al., Human Pathology, vol. 27, No. 2, pp. 111-118, Feb. 1996.

"Implementing a Collaboratory for Microscopic Digital Anatomy", by Stephen J. Young, et al., published in The International Journal of Supercomputer Applications and High Performance Computing, vol. 10, No. 2/3, pp. 170-181, Summer/Fall 1996.

"Proceedings of the International Conference of Telepathology", Double Tree Hotel, Rockville, Maryland, USA, Dec. 5-7, 1996.

"WebSlide Browser, A Thin Client Browser for Internet/Intranet Microscopy", three-page Web site printout from http://web.archive.org/web/19900429034329/http://www.mcs.net/.about.bacus-lab/WebSlide.html, Copyright .COPYRGT. 1998 Bacus Laboratories, Inc.

Search Report from the European Patent Office, re "Remote Controlled Examination of Pathology Specimens", Jul. 18, 2003 addressed to Jeffer, Mangels, Butler & Marmaro, LLP, Attn. Mr. David J. Meyer, Jul. 22, 1999.

CMDA GridManager, Computer Printout, printed May 30, 2002.

"ORNL 's Telepresence Connects Researcher with Remote Microscope", Press Release, from http://www.ornl.gov/Press.sub.--Releases/archive/mr19960627-01.html, printed Jun. 14, 2002.

"Apollo Software Inc.", Advertising Material, printed Jun. 24, 2002.

"Telemedicine Project in the Azores Islands", by L. Concalves and C. Cunha, Arch. Anat. Cytol. Path., pp. 285-287, 1995.

"Bruk av telekommunikasjon i patologisk-anatomisk service", Klinikk og forskning, Tidsskr Nor Lageforen nr., 1, 111:17-19,1991.

Health Care Financing Administration (HCFA) and Reimbursement in Telemedicine, by Helen L Smits and Abby Baum, Journal of Medical Systems, vol. 19, No. 2, 1995.

"Telepathlogy. Long-Distance Diagnosis", by Ronald S. Wenstein, M.D., Kenneth J. Bloom, M.D., and L. Susan Rozek, R.N., A.J.C.P., Apr. (Supp. 1), 1999.

Search Results: "Use of Telecommunications in Pathology and Anatomy Services", by Eide TJ, Nordrum I, Engum B., Rinde E., Patologisk-anatomisk avdeling, Tromso., Tidsskr Nor Laegeforen nr.1, 1991, 111: 17-19.

"Quantitative DNA Analysis: A Comparison of Conventional Dna Ploidy Analysis and Teleploidy", by K.L. Phillips, L. Anderson, Th. Gahm, L.B. Needham, M.L. Goldman, B.E. Wray, T.F. Macri, Arch. Anat. Cytol. Path., pp. 288-295, 1995.

"The Design and Use of a Computer-Based Digital Image Acquisition, Management, and Communications Systems for Conferencing in Pathology", by B.E. Wray and M. Lai-Goldman, pp. 271-274, Arch. Anat. Cytol. Path., vol. 43, No. 4, 1995.

"Multimedic System for Telepathology and Interdisciplinary Councils Between Doctors and Various Hospitals", by H.A. Richter, M. Danaei, N. Maurin, and C. Mittermayer, pp. 296-299, Arch. Anat. Cytol. Path., vol. 43, No. 4, 1995.

"Concept of Telepathology in Croatia", Z. Danilovkc, A. Dzubur, and S. Seiwerth, pp. 282-284, Arch. Anat. Cytol. Path., vol. 43, No. 4, 1995.

"Pathology Consultation Services Via The Arizona-International Telemedicine Network", by R.S. Weinstein, A. Bhattacharyya, Y.P. Yu, J.R. Davis, J.M. Byers, A.R. Graham, R. Martinez, pp. 219-226, Arch. Anat. Cytol. Path., vol. 43, No. 4, 1995.

"Fiabilite Du Diagnostic Anatomo-Pathologique Par Transmission D'Images Statiques", by A. Vieillefornd, F. Staroz, M. Fabre, P. Pedossa, V. Martin-Pop, E. Martin, C. Got, and B. Franc., pp. 246-250, Arch, Anat. Cytol. Path., vol. 43, No. 4, 1995.

"Experience With Distant Pathology Demonstrations for Clinicians in Hospitals Without Local Pathologiest Through the Swedish Telepathology Work Station", by B.R.G. Boeryd, pp. 266-267, Arch. Anat. Cytol. Path., vol. 43, No. 4, 1995.

"Telecytoconsultation: Application Du Systeme Transpath a la Pathologie Cervico-Vaginale", by M.C. Vacher-Lavenue and C. Marsan, pp. 262-265, Arch. Anat. Cytol. Path., vol. 43, No. 4, 1995.

"Aspects of Telepathology in Routinary Diagnostic Work With Specific Emphasis on ISDN", by K. Jayser, P. Fritz and M. Drlicek, pp. 216-218, Arch. Anat. Cytol. Path., vol. 43, No. 4, 1995.

"Telemicroscopy Stations for Telepathology Based on Broadband and ISDN Connections", by P. Schwarzmann, J. Schmid, C. Schnorr, G. Strble, and S. Witte, pp. 209-215, Arch. Anat. Cytol. Path., vol. 743, No. 4, 1995.

"Remote Frozen Section Service in Norway", by I. Nordrum and T.J. Eide, pp. 253-256, Arch. Anat. Cytol. Path., vol. 43, No. 4, 1995.

"Telepathology in Europe, It's Practical use", by K Kayser, pp. 196-199, Arch. Anat. Cytol. Path., vol. 43, No. 4, 1995.

"Adult Multiocular Cyst and Nephroblastomatosis", by O. Ferrer-Roca, A. Sanroman, and J.H. Rodriguez, pp. 234-236, Journal of Telemedicine and Telecare, 1995.

"A Pilot Study of the Physician Acceptance of Tele-oncology", by Ace Allen, Jeanne Haves, Raj Sadasivan, Stephen K. Williamson, and Connie Wittman, pp. 34-37, Journal of Telemedicine and Telecare, 1995.

"Computers in Radiology, Making Global Telemedicine Practical and Afforable: Demonstrations from the Middle East", by Mark A. Goldberg, Hassan S. Sharif, Daniel I. Rosenthal, Stephen Black-Schaffer, Thomas J. Flotte, Robert B. Colvin, and James H. Thrall, pp. 1495-1500, AJR, 1994.

"Current Status of Telepathology", by Tor J. Eide and Ivar Nordrum, pp. 881-890, APMIS 102,1994.

"Telepathology With an Integrated Services Digital Network—A New Tool for Image Transfer in Surgical Pathology: A Preliminary Report", by Martin Oberholzer, M.D., Hans-Rudolf Fischer, et al., pp. 1078-1085, Human Pathology, vol. 24, No. 10, Oct. 1993.

"Use of Remote Video Microscopy (Telepathology) as an Adjunct to Neurosurgical Frozen Section Consultation", by R.L. Becker, Jr., M.D., Ph.D., et al., pp. 909-911, Human Pathology, vol. 24, No. 8, Aug. 1993.

"Legal Aspects of Telepathology", by M. Schiffer, pp. 393-394, Zentralbl. Pathol. 138,1992.

"Aspects of Standardization in Telepathology", by K. Kayser and P. Schwarzmann, pp. 389-392, Zentralbl. Pathol. 138, 1992.

"Telepathology in Sweden, A National Study Including all Histopathology and Cytology Laboratories", pp. 429-430, Zentralbl. Pathol. 138, 1992.

"Human Performance Studies of the Video Microscopy Component of a Dynamic Telepathology System", by Ronald S. Weinstein, Kennth J. Bloom, Elizabeth A. Krupinski, and L. Susan Rozek, pp. 399-401, Zentralbl. Pathol. 138, 1992.

"Telepathology—Visual Telecommunication in Pathology, An Introduction", pp. 381-382, Zentralbl. Pathol. 138, 1992.

"Experience and Present Status of Telepathology in the National Cancer Center Hospital, Tokyo", by Yukio Shimosato, Yukako Yagi, et al., pp. 413-417, Zentralbl. Pathol. 138, 1992.

"Telepathology: A New Tool of Pathology? Presentation of a French National Network", by Etienne Martin, Pierre Dusserre, et al., pp. 419-423, Zentralbl. Pathol. 138, 1992.

"Telepathology in Greece, Experience of the Metaxas Cancer Institute", by G. Miagulis, E. Protopapa, et al., pp. 425-428, Zentralbl. Pathol. 138, 1992.

"Telemicroscopy Design Considerations for a Key Tool in Telepathology", by P. Schwarzmann, pp. 183-187, Zentralbl. Pathol. 138, 1992.

"Remote Frozen Section Service: A Telepathology Project in Northern Norway", by Ivar Nordrum, M.D. Bjorn Engum, M.S., et al., pp. 514-518, Human Pathology, vol. 22, No. 6, Jun. 1991.

"Telepathology Comes of Age in Norway", by Ronald S. Weinstein, M.D., Human Pathology, vol. 22, No. 6, Jun. 1991.

HISTKOM Telepathology, "The Project HISTKOM at the Institut Fur Physikalische Elektronik", http://www.uni-stuttgart.de:80/ipe/res/ip/histkome.htm, Jul. 22, 1999, 4 pages.

"The CAS 200 .TM. MultiScan.TM. Automated Pathology Workstation", by James V. Bacus, from Becton Dickinson Cellular Imaging Systems, Elmhurst, Illinois 60126., 1994.

"Telepathology in France, Justifications and developments", by E. Martin, et al., pp. 191-195, Arch. Anat. Cytol. Path., vol. 43, No. 4, 1995.

Published International Search Report for Serial No. WO 02/056256, dated Jan. 28, 2002, 2 Pgs.
Published International Search Report for Serial No. WO 02/056084, dated Jan. 28, 2002, 2 Pgs.
File History for U.S. Appl. No. 09/323,371, filed Jun. 1, 1999.
File History for U.S. Appl. No. 10/448,913, filed May 30, 2003.
File History for U.S. Appl. No. 11/485,478, filed Jul. 12, 2006.
File History for U.S. Appl. No. 11/485,005, filed Jul. 12, 2006.
File History for U.S. Appl. No. 10/620,016, filed Jul. 14, 2003.
File History for U.S. Appl. No. 11/520,816, filed Aug. 11, 2006.
File History for U.S. Appl. No. 12/118,356, filed May 9, 2008.
File History for U.S. Appl. No. 12/403,275, filed Mar. 12, 2009.
File History for U.S. Appl. No. 12/459,184, filed Jun. 26, 2009.
File History for U.S. Appl. No. 12/584,365, filed Sep. 3, 2009.

* cited by examiner

1. Images are moved relative to one another in fixed increments in both the x and y axes (search region).

2. At each search position, correlation (or other measure of goodness of overlap) is calculated.

3. Search position with best correlation used to join images together.

ated sysTEMS AND METHODS
INTERGRATED SYSTEMS AND METHODS OF VIRTUAL OR LIVE MICROSCOPE SLIDE PRESENTATION

RELATED APPLICATION

This application is a continuation of application Ser. No. 10/620,016 filed Jul. 14, 2003, which in turn is a continuation-in-part of application Ser. No. 10/448,913 filed May 30, 2003, now U.S. Pat. No. 7,228,839 issued May 29, 2007, which in turn is a continuation of Ser. No. 09/323,371, filed Jun. 1, 1999, now U.S. Pat. No. 6,606,413 issued Aug. 12, 2003, which claims the benefit of U.S. Provisional Application No. 60/087,523 filed Jun. 1, 1998, all of the aforementioned applications and patents being hereby fully incorporated herein by reference.

BACKGROUND OF THE INVENTION

This invention relates to a method and apparatus for viewing remote microscope images.

Currently there is increasing demand for pathologist review of samples at remote locations. There exist multiple systems to address this need. They typically fall within one of two categories: live remote microscopy and virtual slide imaging.

In live remote control microscopy, a user receives images that are taken from a slide on a microscope. In virtual slide imaging, a user receives images previously captured. Virtual slide systems take one or more images of an area of interest and assemble them together (if there is more than one image) to form a virtual slide. Each of these techniques has its advantages. Live remote imaging provides users with the closest approximation to manual manipulation. Virtual slides allow faster image viewing, since images are already captured.

Virtual slide systems take one or more images and assemble them to form a "virtual slide."

However, users in the past were limited in their ability to integrate these technologies. One could only view and manipulate live and virtual images independently of one another. A user would have to clumsily go back and forth between these two modes of operation to separately look at the virtual slides and live microscope slides. We present a new method that integrates these ideas into one seamless operating environment.

SUMMARY OF THE INVENTION

In accordance with the present invention, a method and apparatus are provided for the analysis of remote slides in a hybrid live and virtual medium. Users obtain benefits of each technique in a unified environment.

While the apparatus and methods of the present invention have been illustrated in terms of certain embodiments, the invention claimed herein is not limited to embodiments disclosed in this application. Rather, the scope of the invention is defined by the claims attached hereto.

While the invention has been illustrated and explained herein in terms of certain embodiments the invention is not limited to the specific embodiments disclosed. Rather, the invention is defined by the scope of the claims appended hereto.

DETAILED DESCRIPTION OF THE PREFERRED EMBODIMENT

A virtual slide is a digital representation of an area of interest of a microscopic slide. A virtual slide can be created multiple ways.

Figure 1:
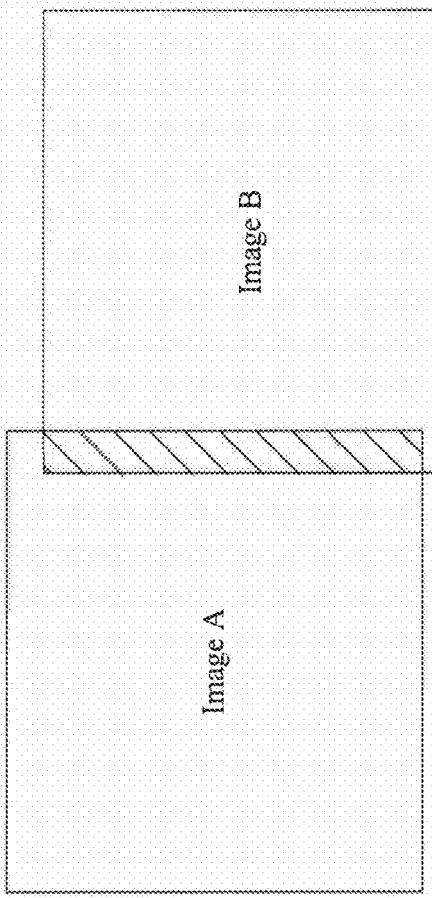
FIG. 1 is a drawing showing the overlap between adjacent images during optimization of overlap.
Figure 1:
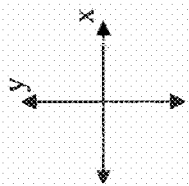

One method is to use a motorized microscope that can move a specimen with respect to a microscope objective (e.g., a microscope with a motorized stage). With such system, one can capture one or more images through a microscope objective, such that a region of interest (all or part of the microscopic slide) is imaged. Each image is then joined together to form a composite or "virtual image." Multiple methods of joining images together are known in the art. One example is when images are simply abutted one next to another. However, this method does not generally produce virtual slides without seams, because errors such as camera rotation relative to the axis of motion are difficult to correct. Even with submicron accuracy stages it is, in practice, difficult to obtain consistent positioning. Another method is to utilize overlap between adjacent images to edge align images for maximum seamlessness. This can be done by sequentially shifting overlapping regions in the x and/or y axis, for example, by a stepping motor, and calculating a correlation value (or measure of goodness of overlap). The shift which results in the best correlation value is then used to join the images together (FIG. 1). While this method can be computationally expensive, it reduces reliance on difficult-to-attain mechanical positioning, requirements and ultimately produces the best images in the sense of seamlessness.

In another method, the virtual slide is made simply by utilizing an imaging device with optics suitable to take a an image of the area of interest on the slide in one snapshot. This method is embodied in the form of a conventional digital or analog camera with a macro lens.

This virtual slide can then be used to create a thumbnail view of the slide. To create the thumbnail view, the virtual slide is shrunk in resolution from its original, base resolution to a target resolution. If the target resolution is the same as the base resolution, then the image is unchanged. However, typically the resolution of the thumbnail desired is several times smaller than the base resolution.

Figure 2:
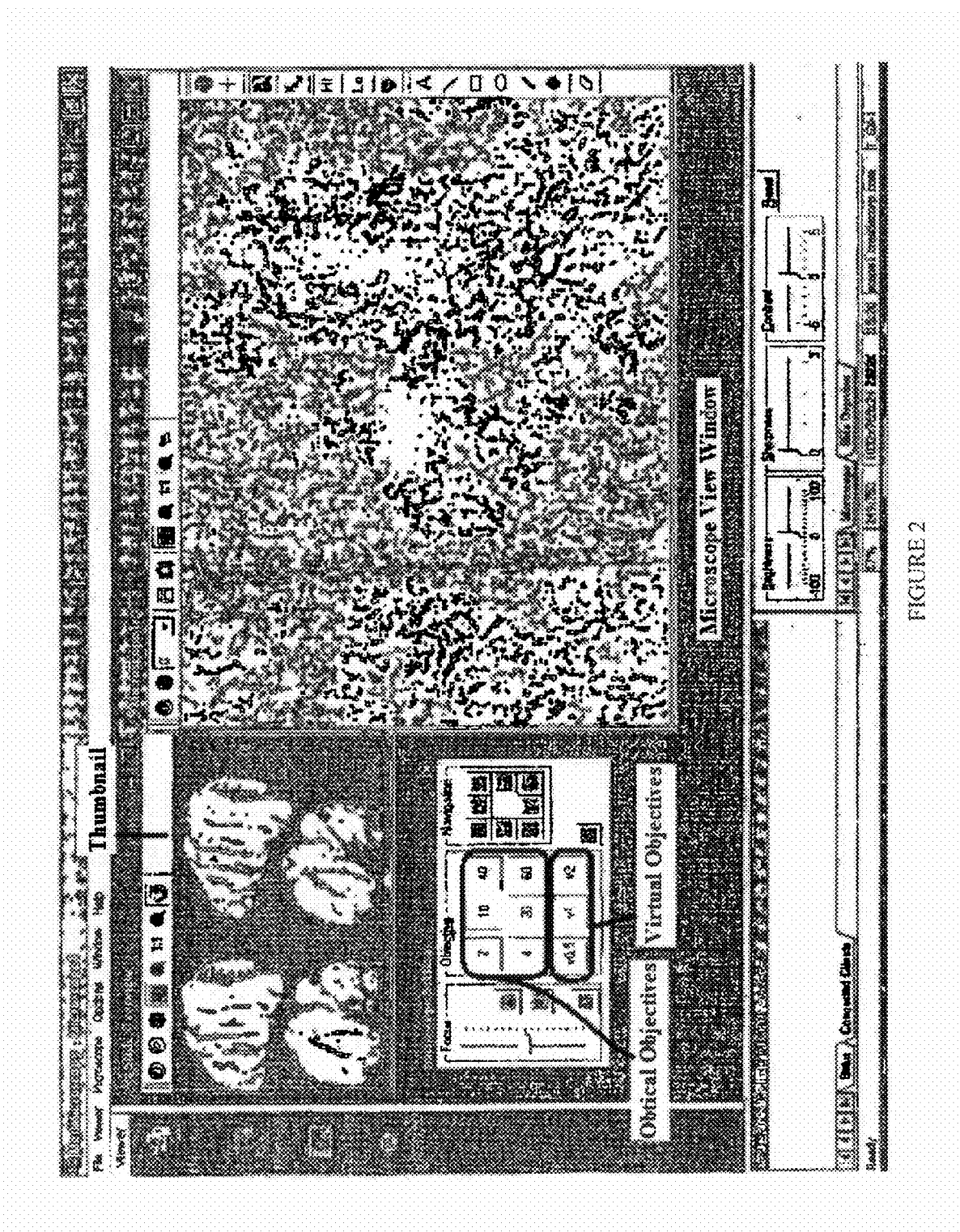
FIG. 2 is a photograph of a user's view of the remote microscope, showing a thumbnail view, microscope imaging window, and a set of microscope controls.

With the virtual slide created, the user may fully utilize the full capabilities of the remote microscope. The user is presented with an image window and a set of control features (FIG. 2). Among these control features is a set of "optical objectives" and "virtual objectives."

Optical objectives are images that are created by a camera digitizing an image through a microscope objective (e.g., 10.times., 20.times., or 40.times.) in real time (i.e., an image is captured at the time the user requests the image). Virtual objectives are digitally created magnifications created not by digitizing in real time, but rather by utilizing the existing virtual slide data to digitally create a field of view.

When a user selects one of the optical objectives, a "change objective" command is sent to the microscope. This change objective command can also, specify additional qualifying information, such as microscope x, y, z positions, exposure setting, compression type and level, and image dimensions. If additional qualifying information is not sent, then the implicit qualifying information is the current state of the microscope or the last specified state. When the microscope receives the command, actions are taken to change the objective lens and to change the state of the microscope commensurate with the command (e.g., change the relative position of the objective lens relative to the microscopic slide, change exposure, etc.). An image is then digitized, compressed if so specified, and then transmitted to the user for display.

When a user selects a virtual objective, a virtual objective command is sent to the microscope. Similar to an optical objective command, this virtual objective command can also specify additional qualifying information, such as microscope x, y, and/or z position. If additional qualifying information is not sent, then the implicit qualifying information is current microscope state or the last specified state. A region of interest is defined by the virtual request—it is the area on the microscope slide included in the field specified by the coordinates of the stage x, y and magnification of the command. This region of interest may optionally be trimmed such that image information already residing at the requesting user's, view is not retransmitted to the user.

An image of the region of interest can be created from the virtual slide in multiple ways. If the virtual slide is not compressed, the retrieval of image information corresponding to the region of interest can be done by simply copying data from the virtual slide. If the virtual slide is compressed, a region corresponding to at least the region of interest can be decompressed to a raw bitmap from the main compressed image. If the virtual slide was stored as multiple compressed images rather than one large image, additional efficiencies are possible. For example, only those images that contain the desired region of interest need be accessed for decompression, rather than the entire area of the virtual slide. This enhances performance.

The decompression itself can also be performed in various ways. Strategies such as scaled decoding, as in the case of jpeg type compression, can be employed to improve the speed of the decompression by coupling a resolution reduction process with the decompression to speed up decompression when resolution reduction is required. Once the region of interest is decompressed, it can then be recompressed using a variety of strategies known to those skilled in the imaging field, which need not be the same as the method by which the virtual slide was compressed.

An alternative type of decompression/recompression step can also be used involving partial decompression. Partial decompression, such as decoding of Huffman-encoded data, as in the case of jpeg, can be performed to produce raw coefficients, rather than full decompression, which produces a raw bitmap. The raw coefficients corresponding to the area of the region of interest can then be selected. These coefficients which correspond to the region of interest are then re-encoded. In the case of jpeg compression, this would involve re Huffman encoding of the coefficients, rather than in normal full compression, where a dct must be performed followed by quantization and then Huffman coding.

Whichever the technique, the result is a compressed region of interest. The compressed region of interest is then transmitted to the user for viewing. The described method is more advantageous than sending the entire virtual slide, as one efficiently sends only that information required by the user.

However, direct transfer of the compressed image without decompression is feasible when the virtual slide is stored as multiple compressed images. The compressed images that include the area specified by the region of interest can be directly transferred to the user, rather than going through a decompression/recompression step. The disadvantage is that one may transfer more information than is needed if, for example, the compressed images are at a higher resolution that the requested resolution. This can be partially solved by creation of multiple resolution versions of the virtual slide.

There are also compression strategies available that allow only portions of the compressed images to be sent, such that a given resolution can be attained depending on which portions of the compressed image one chooses to send (e.g., progressive encoding). However, there is still the issue that the region of interest only partially covers the area of the compressed image. In this case, direct transfer of the image results in inefficiently sending data including both the region of interest and data outside the region of interest to the user.

With this invention, users are afforded a streamlined method of utilizing the features of virtual and live microscopy techniques.

The invention claimed is:

1. A computer implemented method for presenting an image to a user of a specimen on a microscope slide on an electronic display screen, said method comprising:

using a microscope to capture a plurality of images of the microscope slide, each of the captured images corresponding to a magnification;

providing, on the electronic display screen, at least one previously-captured image from the plurality of images of said microscope slide to the user;

presenting a plurality of selectable objectives on the electronic display screen for viewing said microscope slide, the plurality of selectable objectives including at least a first objective identifying a first magnification of the plurality of previously captured image magnifications and at least a second objective identifying a second magnification different from the first magnification that is not a magnification matching the magnification of any of the plurality of previously captured images;

accepting a selection from the user of one of the plurality of selectable objectives, said selected objective corresponding to the desired magnification; and if the selected objective is identified as having the same magnification of one of the plurality of previously-captured images, displaying the one of the plurality of previously-captured images having the same magnification as the selected objective on the electronic display screen, and if the selected objective is not identified as having the same magnification as one of the plurality of previously-captured images, using the microscope to obtain a real-time image of the microscope slide at the desired magnification, and displaying the real-time image having the desired magnification on the electronic display screen.

2. The method of claim 1, wherein the plurality of images comprises multiple compression levels.

3. The method of claim 1, wherein the at least one previously-captured image is a compressed image, the method further comprising creating a region of interest including selecting and decompressing a portion of the at least one previously-captured image.

4. The method of claim 3, further comprising transmitting the region of interest to the user.

5. The method of claim 3, further comprising recompressing the region of interest.

6. The method of claim 5, further comprising transmitting the region of interest to the user.

7. The method of claim 1, wherein the at least one previously-captured image comprises a plurality of compressed images, the method further comprising creating a region of interest including selecting and decompressing a portion of one or more of the compressed images.

8. The method of claim 7, further comprising transmitting the region of interest to the user.

* * * * *

UNITED STATES PATENT AND TRADEMARK OFFICE
CERTIFICATE OF CORRECTION

PATENT NO. : 8,036,868 B2  Page 1 of 1
APPLICATION NO. : 12/584831
DATED : October 11, 2011
INVENTOR(S) : Jack A. Zeineh et al.

It is certified that error appears in the above-identified patent and that said Letters Patent is hereby corrected as shown below:

Title Page 2, Item (56), Reference 1, delete "Telepathology" and insert --"Telepathology--;
Title Page 2, Item (56), Reference 1, Line 56-57, delete "services," and insert --services",--;
Title Page 2, Item (56), Reference 6, Line 69, delete "Telepathology" and insert --"Telepathology--;
Title Page 2, Item (56), Reference 6, Line 70, delete "Report," and insert --Report",--;
Title Page 2, Item (56), Reference 11, Line 6, delete "Telepathology" and insert --"Telepathology--;
Title Page 2, Item (56), Reference 11, Line 7, delete "Pathology," and insert --Pathology",--;
Title Page 2, Item (56), Reference 15, Line 17, delete "The" and insert --"The"--;
Title Page 2, Item (56), Reference 15, Line 17, delete "Frozem" and insert --Frozen--;
Title Page 2, Item (56), Reference 15, Line 18, delete "(Telepathology)," and
insert --(Telepathology)",--;
Title Page 2, Item (56), Reference 17, Line 23, delete "l'infomratique" and insert --l'informatique--;
Title Page 2, Item (56), Reference 17, Line 23, delete "telephathologie" and insert --télépathologie--;
Title Page 2, Item (56), Reference 19, Line 28, delete "A" and insert --"A--;
Title Page 2, Item (56), Reference 19, Line 28, delete "Images," and insert --Images",--;
Title Page 2, Item (56), Reference 29, Line 65, delete "Factors" and insert --"Factors--;
Title Page 2, Item (56), Reference 29, Line 66, delete "Mammography,"
and insert --Mammography",--;
Title Page 2, Item (56), Reference 32, Line 74, delete "Telepathology" and insert --"Telepathology--;
Title Page 2, Item (56), Reference 32, Line 74, delete "Internet," and insert --Internet",--;
Title Page 3, Item (56), Reference 11, Line 34, delete ".COPYRGHT.";
Title Page 3, Item (56), Reference 18, Line 49, delete "Health" and insert --"Health--;
Title Page 3, Item (56), Reference 18, Line 50, delete "Telemedicine," and insert --Telemedicine",--;
Title Page 3, Item (56), Reference 27, Line 10, delete "Pathologiest" and insert --Pathologists--;
Title Page 3, Item (56), Reference 32, Line 25, delete "It's" and insert --Its--;
Column 2, Line 33, delete "positioning," and insert --positioning--;
Column 2, Line 54, delete "10.times., 20.times., or 40.times.)" and insert --10×, 20× or 40×)--.

Signed and Sealed this
Twenty-sixth Day of June, 2012

David J. Kappos
*Director of the United States Patent and Trademark Office*